(12) United States Patent
Min et al.

(10) Patent No.: US 8,535,213 B2
(45) Date of Patent: Sep. 17, 2013

(54) VENTRICULAR ASSIST DEVICE

(75) Inventors: Byoung Goo Min, Goyang-si (KR); Jung Chan Lee, Seoul (KR)

(73) Assignee: Libraheart Inc., Jeju-Do (KR)

( * ) Notice: Subject to any disclaimer, the term of this patent is extended or adjusted under 35 U.S.C. 154(b) by 0 days.

(21) Appl. No.: 13/390,087

(22) PCT Filed: Aug. 11, 2010

(86) PCT No.: PCT/KR2010/005264
§ 371 (c)(1),
(2), (4) Date: Mar. 9, 2012

(87) PCT Pub. No.: WO2011/019201
PCT Pub. Date: Feb. 17, 2011

(65) Prior Publication Data
US 2012/0157756 A1 Jun. 21, 2012

(30) Foreign Application Priority Data

Aug. 12, 2009 (KR) .......................... 10-2009-0074339

(51) Int. Cl.
*A61N 1/362* (2006.01)
(52) U.S. Cl.
USPC .......................................................... 600/16

(58) Field of Classification Search
USPC ............................................................ 600/16
See application file for complete search history.

(56) References Cited

U.S. PATENT DOCUMENTS

| | | | |
|---|---|---|---|
| 6,264,601 B1 * | 7/2001 | Jassawalla et al. | 600/16 |
| 2007/0004960 A1 * | 1/2007 | Azzolina | 600/16 |
| 2011/0137107 A1 * | 6/2011 | Vodermayer et al. | 600/16 |

* cited by examiner

*Primary Examiner* — George Manuel
*Assistant Examiner* — Robert N Wieland
(74) *Attorney, Agent, or Firm* — IPLA P.A.; James E. Bame (57) ABSTRACT

A ventricular assist device includes a case, a pair of blood bags and a squeezing unit. The blood bags are installed inside the case. Each of the blood bags includes an inlet port connected to a ventricle of a heart to introduce therethrough blood flowing out from the ventricle, an internal space formed to store the blood introduced through the inlet port and an outlet port connected to an artery to discharge therethrough the blood stored in the internal space. The internal space has a variable volume. The squeezing unit is installed inside the case. The squeezing unit is configured to alternately squeeze the blood bags in such a way that, if one of the blood bags is squeezed to discharge the blood, the other blood bag is inflated to draw the blood.

12 Claims, 9 Drawing Sheets

VENTRICULAR ASSIST DEVICE

FIELD OF THE INVENTION

The present invention relates to a ventricular assist device and, more particularly, to a ventricular assist device that ejects blood to assist the function of a ventricle of a heart failure patient.

BACKGROUND OF THE INVENTION

In general, a ventricular assist device is used in case where a medical treatment is no longer effective to a heart failure patient or in case where it is difficult to treat a heart failure by open heart surgery. The ventricular assist device is employed to replace a ventricle function until heart transplantation become available or to reduce a heart load in a restoration period.

One thirds of the patients having a ventricular assist device go through heart transplantation and one fifths thereof are restored with no heart transplantation. Ventricular assist devices are assorted into an implant-type ventricular assist device and an extracorporeal ventricular assist device depending on the grafted regions. Furthermore, the ventricular assist devices are classified into a left ventricle assist device, a right ventricle assist device and a left-right ventricle assist device depending on the heart portions assisted by the ventricular assist device. The left ventricle assist device is widely used. Moreover, the ventricular assist devices are assorted into a pneumatic type and an electric type depending on the kinds of energy used. In addition, the ventricular assist devices are classified into a pulsating type, a centrifugal type and an axial flow type depending on the kinds of actuators (pumps) that ejects blood. An implant-type left-right ventricle assist device may be regarded as one kind of artificial hearts but differs from a perfectly-transplanted artificial heart through which blood is circulated with a natural heart removed.

Figure 1:
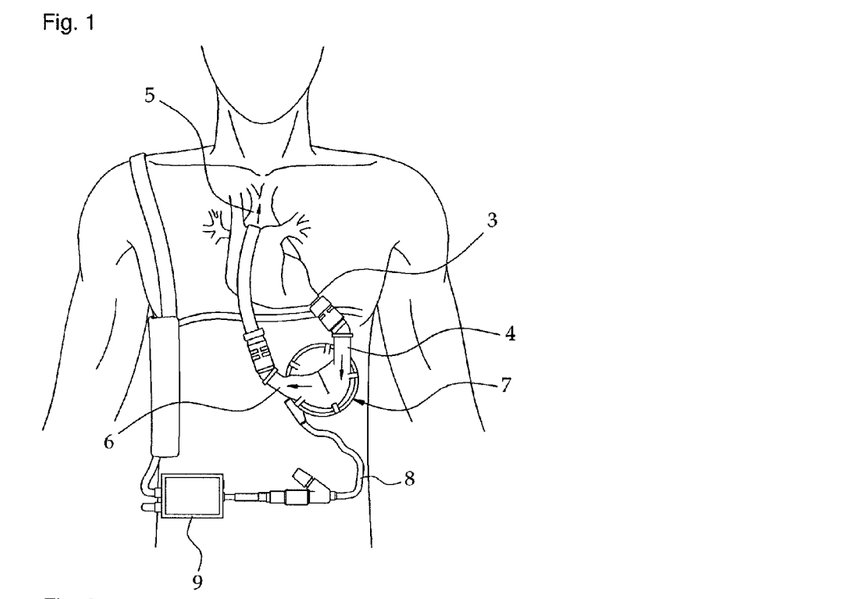
FIG. 1 is a schematic configuration view showing a conventional ventricular assist device.

FIG. 1 shows a representative intracorporeal-type ventricular assist device (HeartMate, a product of Thoratec Corp., U.S.A.). Referring to FIG. 1, the ventricular assist device includes an inlet conduit 4 connected to the top portion 3 of the left ventricle, an outlet conduit 6 connected to the aorta 5 and a blood pump 7 connected to the inlet conduit 4 and the outlet conduit 6. The blood pump 7 includes a blood bag (not shown) connected to the inlet conduit 4 and the outlet conduit 6, a squeezer (not shown) for squeezing the blood bag so that the blood introduced into the blood bag through the inlet conduit 4 can be ejected through the outlet conduit 6, and an electric motor (not shown) connected to the squeezer. One-way valves permitting blood to flow only in one direction are installed in the inlet conduit 4 and the outlet conduit 6. A battery and a control unit 9 are provided outside the body and are connected to the blood pump 7 through electric wires 8 penetrating the skin. The ejection of blood is controlled by the control unit 9. The battery serves to supply electric power to the control unit 9 and the electric motor.

The ventricular assist device cited above is provided with only one blood bag. Therefore, if the blood stored in the blood bag is ejected once, the blood can be ejected again only after the blood is sufficiently gathered in the blood bag. In other words, if the blood bag is squeezed, the volume of the blood bag is reduced whereby the blood flows out from the blood bag but does not flow into the blood bag. To the contrary, if the blood bag is released, the volume of the blood bag is increased due to the elastic restoration of the blood bag whereby the blood flows into the blood bag but does not flow out from the blood bag. In this manner, the inflow and outflow of the blood occurs alternately over time in the conventional ventricular assist device. This poses a problem in that the inflow and outflow of the blood is performed in a quite inefficient manner.

In case of the implant-type ventricular assist device, the volume of the blood bag undergoes a change before and after the blood bag is squeezed. In order to compensate the changed volume, it is necessary to employ a volume compensator or a vent line extending to the outside of the body. In other words, a volume compensator or a vent line for re-inflating the blood bag is needed in order to allow the blood to flow into the blood bag after ejection thereof. Use of the volume compensator or the vent line tends to make the ventricular assist device complex. In particular, the vent line may become a cause of increasing the risk of infection.

SUMMARY OF THE INVENTION

In view of the problems noted above, it is an object of the present invention to provide a ventricular assist device capable of continuously discharging and drawing blood while maintaining the pulsatility of blood.

Another object of the present invention is to provide a ventricular assist device having an improved structure and requiring neither a volume compensator nor a vent line.

According to one aspect of the present invention, there is provided a ventricular assist device, including: a case; a pair of blood bags installed inside the case, each of the blood bags including an inlet port connected to a ventricle of a heart to introduce therethrough blood flowing out from the ventricle, an internal space formed to store the blood introduced through the inlet port and an outlet port connected to an artery to discharge therethrough the blood stored in the internal space, the internal space having a variable volume; and a squeezing unit installed inside the case, the squeezing unit configured to alternately squeeze the blood bags in such a way that, if one of the blood bags is squeezed to discharge the blood, the other blood bag is inflated to draw the blood.

In the ventricular assist device of the present invention, a pair of blood bags is used to assist a ventricle function. This makes it possible to efficiently draw and discharge blood. It is also possible to continuously draw blood while keeping the pulsatility of blood and to supply an increased amount of pulsatile blood. Accordingly, it is possible to prevent the blood from being instantaneously stagnant and to effectively increase the flow rate of the blood.

Inasmuch as the ventricular assist device is configured to alternately squeeze the blood bags, there is no need to employ a volume compensator or a vent line. This helps simplify the structure of the ventricular assist device, thereby significantly enhancing the reliability and the durability of the ventricular assist device. In addition, it is possible to save the manufacturing cost of the ventricular assist device and to sharply reduce the risk of infection.

BRIEF DESCRIPTION OF THE DRAWINGS

The above and other objects and features of the present invention will become apparent from the following description of preferred embodiments, given in conjunction with the accompanying drawings.

DETAILED DESCRIPTION OF THE PREFERRED EMBODIMENTS

Certain preferred embodiment of the present invention will now be described in detail with reference to the accompanying drawings.

FIGS. 2 through 8 show a ventricular assist device according to one embodiment of the present invention. Referring to FIGS. 2 through 8, the ventricular assist device 100 according to one embodiment of the present invention includes an inlet connector 10, a first blood bag 21, a second blood bag 22, an outlet connector 30, a first inlet valve 41, a second inlet valve 42, a first outlet valve 51, a second outlet valve 52, a squeezing unit, an electric motor 70 and a case 80.

Figure 2:
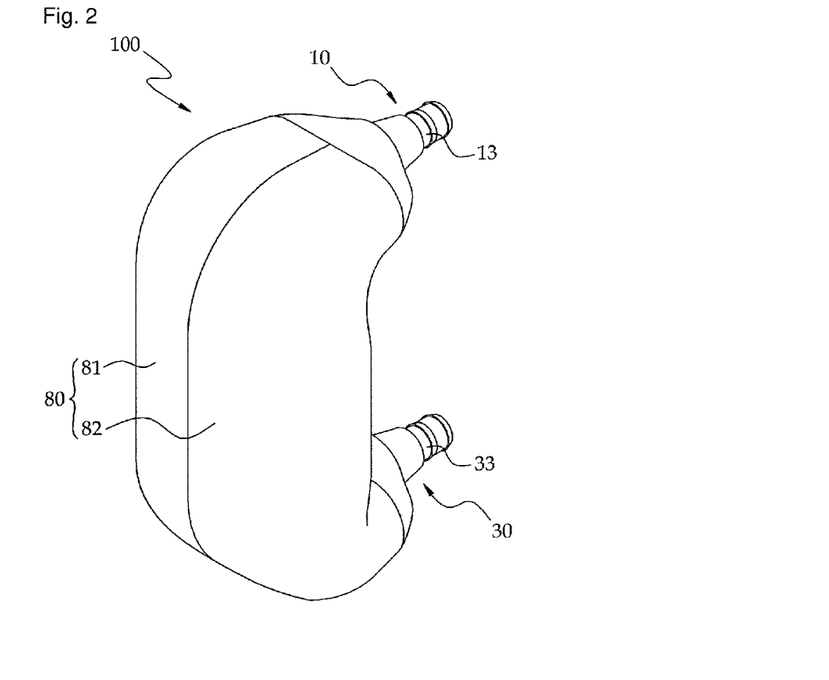
FIG. 2 is a schematic perspective view showing a ventricular assist device according to one embodiment of the present invention.
Figure 3:
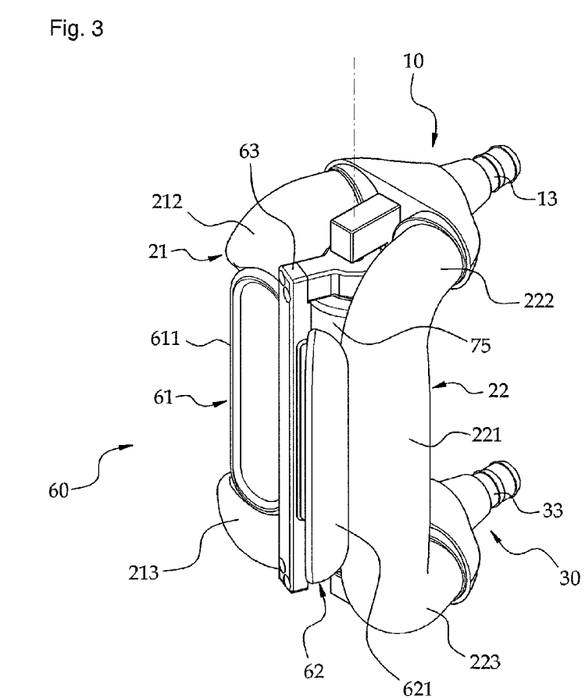
FIG. 3 is a perspective view of the ventricular assist device shown in FIG. 2 with a case removed for clarity.

The inlet connector 10 is made of a medical-purpose polymeric material or a metal alloy having superior biocompatibility. The inlet connector 10 is connected to a ventricle 1, e.g., a left ventricle or a right ventricle, of the heart via an inlet conduit 14. The opposite end portions of the inlet conduit 14 are inserted into the ventricle 1 and the connecting portion 13 of the inlet connector 10. The inlet conduit 14 is formed of an artificial blood vessel or a medical catheter having superior biocompatibility.

The inlet connector 10 includes an inlet flow path (not shown), a first outlet flow path 11 and a second outlet flow path 12. The inlet flow path is formed inside the connecting portion 13. The inlet flow path is connected to the inlet conduit 14 and serves as a passageway through which blood is introduced from the ventricle 1. The first outlet flow path 11 and the second outlet flow path 12 are formed independently of each other and are connected to the inlet flow path. Thus the blood introduced through the inlet flow path can flow into the first outlet flow path 11 and the second outlet flow path 12.

The first blood bag 21 and the second blood bag 22 are made of a flexible material. More specifically, the first blood bag 21 and the second blood bag 22 are made of a biopolymer, e.g., medical-purpose polyurethane, which is pliant and is superior in blood compatibility and durability. The internal spaces of the first blood bag 21 and the second blood bag 22 can be changed in volume. Such change in volume are caused by squeezing the first blood bag 21 and the second blood bag 22 with the squeezing unit to be described later. If necessary, the change in volume may be caused by inflating or deflating first blood bag 21 and the second blood bag 22 so that the surface areas thereof can be increased or decreased. The opposite ends of each of the first blood bag 21 and the second blood bag 22 are opened. A space for storing the blood is formed within each of the first blood bag 21 and the second blood bag 22. One open end portion of each of the first blood bag 21 and the second blood bag 22 is connected to each of the first outlet flow path 11 and the second outlet flow path 12. The blood flowing out from the first outlet flow path 11 and the second outlet flow path 12 is stored in the first blood bag 21 and the second blood bag 22.

The first blood bag 21 includes a first cylinder portion 211 formed into a generally cylindrical shape and a pair of joint portions 212 and 213 joined to the first cylinder portion 211 at a specified angle. Just like the first blood bag 21, the second blood bag 22 includes a second cylinder portion 221 and a pair of joint portions 222 and 223. The first cylinder portion 211 and the second cylinder portion 221 are arranged parallel to each other.

The outlet connector 30 is made of a medical-purpose polymeric material or a metal alloy having superior biocompatibility. The outlet connector 30 is connected to an artery 2, e.g., an aorta or a pulmonary artery, via an outlet conduit 34. The opposite end portions of the outlet conduit 34 are inserted into the artery 2 and the connecting portion 33 of the outlet connector 30. The outlet conduit 34 is formed of an artificial blood vessel or a medical catheter having superior biocompatibility.

The outlet connector 30 includes a first inlet flow path 31 and a second inlet flow path 32 and an outlet flow path (not shown). The first inlet flow path 31 and the second inlet flow path 32 are formed independently of each other and are connected to the other open portions of the first blood bag 21 and the second blood bag 22. The outlet flow path is formed inside the connecting portion 33. The outlet flow path is connected to the first inlet flow path 31 and the second inlet flow path 32. The blood ejected from the first blood bag 21 or the second blood bag 22 flows through the first inlet flow path 31 or the second inlet flow path 32. Thereafter, the blood is supplied to the artery 2 through the outlet flow path and the outlet conduit 34.

The first inlet valve 41 and the second inlet valve 42 are installed in the first outlet flow path 11 and the second outlet flow path 12 of the inlet connector 10. The first inlet valve 41 and the second inlet valve 42 are one-way valves that permit the blood to flow only in one direction. More specifically, the first inlet valve 41 permits the blood to flow from the inlet flow path of the first inlet valve 41 toward the first blood bag 21 but prevents the blood from flowing in the reverse direction. The second inlet valve 42 permits the blood to flow from the inlet flow path of the second inlet valve 42 toward the second blood bag 22 but prevents the blood from flowing in the reverse direction. The first inlet valve 41 and the second inlet valve 42 are formed of, e.g., a valve made of a medical-purpose polymeric material having superior biocompatibility, a mechanical prosthetic valve or a tissue valve.

The first outlet valve 51 and the second outlet valve 52 are installed in the first inlet flow path 31 and the second inlet flow path 32. The first outlet valve 51 and the second outlet valve 52 are one-way valves that permit the blood to flow only in one direction. More specifically, the first outlet valve 51 permits the blood to flow from the first blood bag 21 toward the outlet flow path of the outlet connector 30 but prevents the blood from flowing in the reverse direction. The second outlet valve 52 permits the blood to flow from the second blood bag 22 toward the outlet flow path of the outlet connector 30 but prevents the blood from flowing in the reverse direction. The first outlet valve 51 and the second outlet valve 52 are formed of, e.g., a valve made of a medical-purpose polymeric material having superior biocompatibility, a mechanical prosthetic valve or a tissue valve.

The squeezing unit serves to alternately squeeze the first blood bag 21 and the second blood bag 22. The squeezing unit includes a squeezer 60 and an electric motor 70. The squeezer 60 is configured to alternately squeeze the first blood bag 21 and the second blood bag 22, thereby ejecting the blood stored in the respective blood bags. Since the squeezer 60 continues to squeeze one of the first blood bag 21 and the second blood bag 22, the blood is ejected at all times. More specifically, the squeezer 60 alternately squeezes one of the first blood bag 21 and the second blood bag 22 in such a way that the blood flows out from one of the blood bags 21 and 23 squeezed while flowing into the other blood bag inflated.

Figure 6:
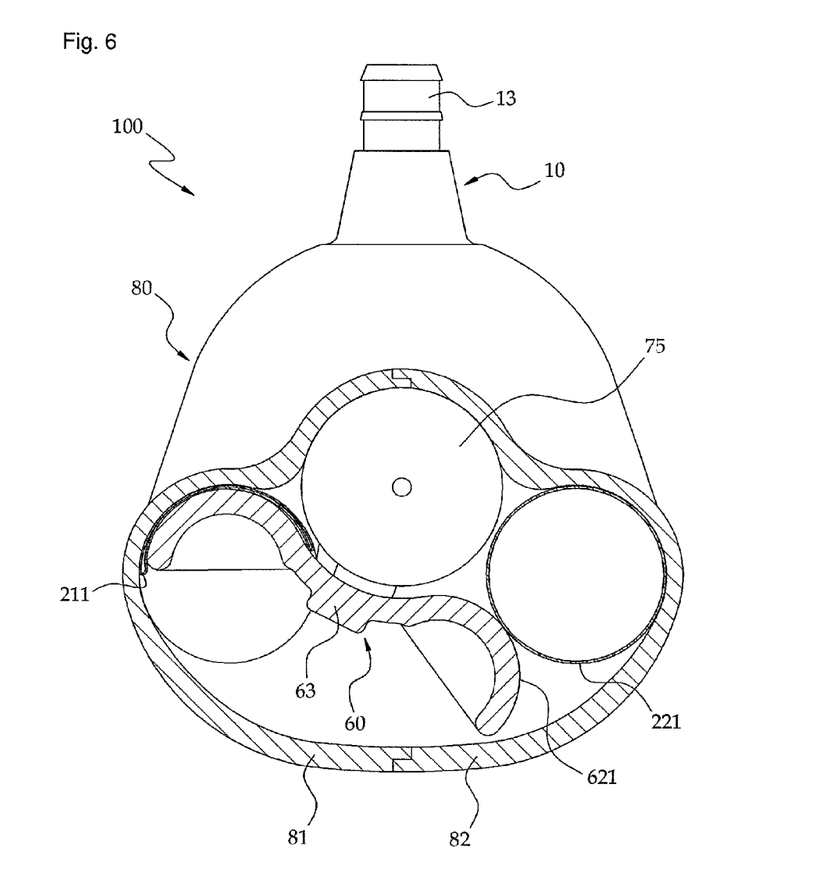
FIGS. 6 and 7 are schematic partial section views for explaining the operating process of the ventricular assist device shown in FIG. 2.
Figure 7:
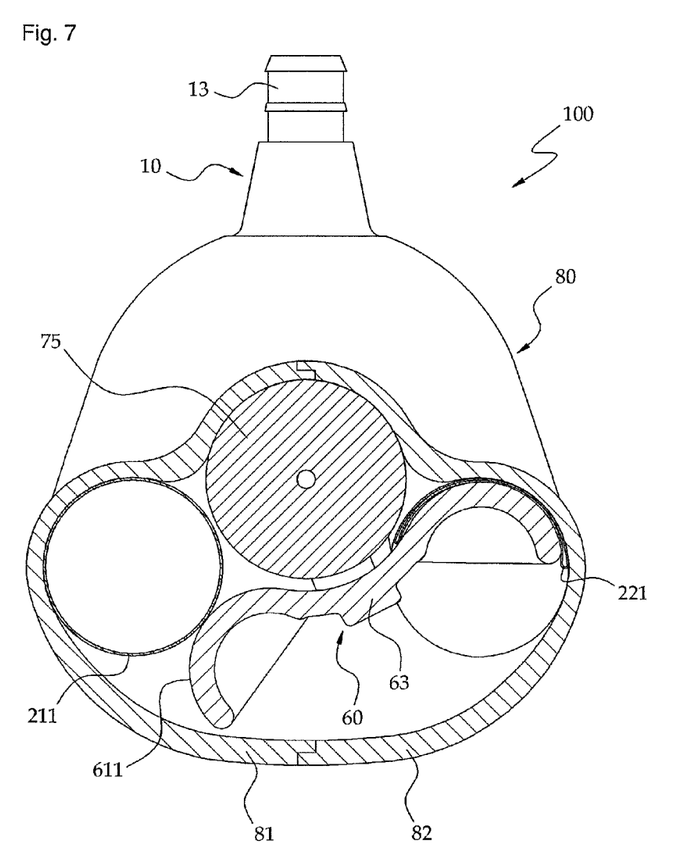
Figure 8:
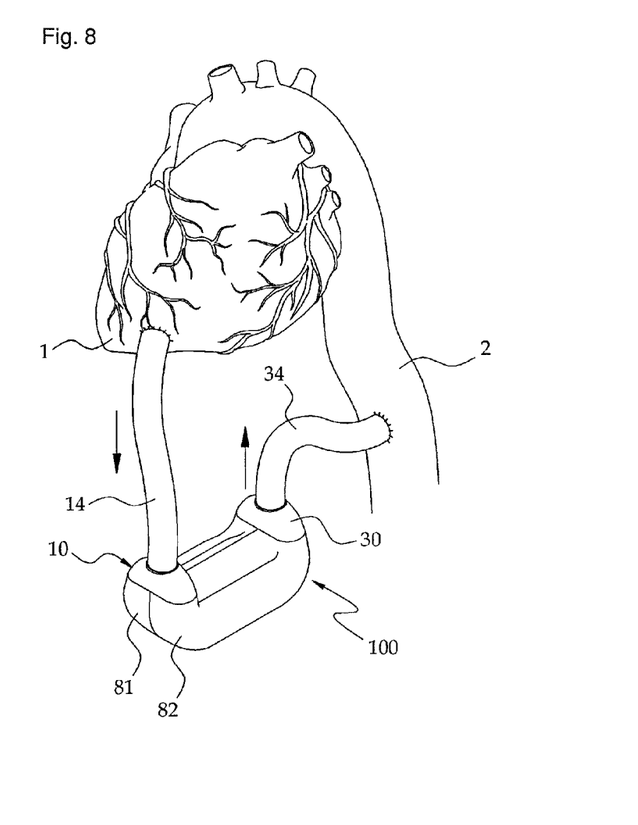
FIG. 8 is a perspective view schematically showing how the ventricular assist device shown in FIG. 2 is installed within a human body.

The squeezer 60 includes a first squeezing portion 61, a second squeezing portion 62 and a connecting portion 63. The first squeezing portion 61 and the second squeezing portion 62 are arranged to squeeze the first blood bag 21 and the second blood bag 22, respectively. In other words, if the first squeezing portion 61 squeezes the first cylinder portion 211 of the first blood bag 21 as shown in FIG. 6, the second squeezing portion 62 does not squeeze the second cylinder portion 221 of the second blood bag 22. In contrast, if the second squeezing portion 62 squeezes the second cylinder portion 221 of the second blood bag 22 as illustrated in FIG. 7, the first squeezing portion 61 does not squeeze the first cylinder portion 211 of the first blood bag 21. In this manner, the first blood bag 21 and the second blood bag 22 are alternately squeezed in response to the operation of the squeezer 60. Thus the blood is ejected continuously.

The surfaces of the first squeezing portion 61 and the second squeezing portion 62 are formed into a curved surface shape bulging toward the each of the first blood bag 21 and the second blood bag 22. This is advantageous in completely ejecting the blood stored in the first blood bag 21 and the second blood bag 22.

Figure 4:
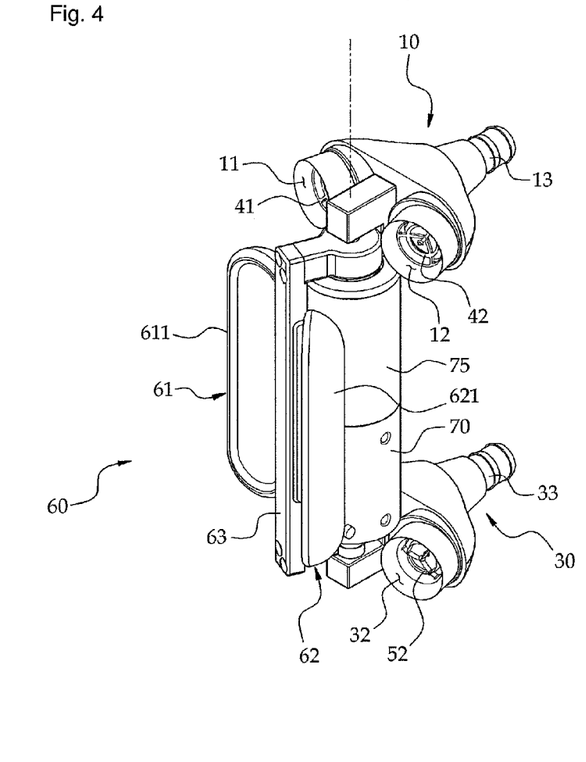
FIGS. 4 and 5 are perspective views of the ventricular assist device shown in FIG. 3 with blood bags removed for clarity.
Figure 5:
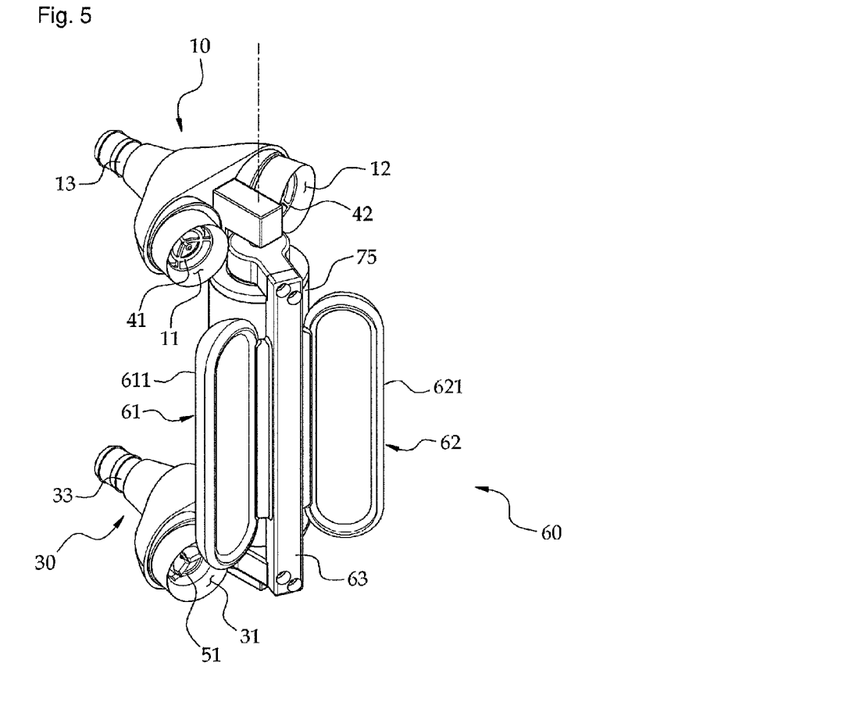

The surfaces of the first squeezing portion 61 and the second squeezing portion 62 making contact with the first blood bag 21 and the second blood bag 22 include a first bulging portion 611 and a second bulging portion 621, respectively. The first bulging portion 611 and the second bulging portion 621 extend in one longitudinal direction, namely parallel to the longitudinal direction of the first cylinder portion 211 and the second cylinder portion 221. The first bulging portion 611 and the second bulging portion 621 are parallel to each other and parallel to the first cylinder portion 211 and the second cylinder portion 221. Each of the first bulging portion 611 and the second bulging portion 621 has a substantially semicircular cross section taken along a plane perpendicular to the longitudinal direction.

The first squeezing portion 61 and the second squeezing portion 62 may be adhesively fixed to the first blood bag 21 and the second blood bag 22. If the first squeezing portion 61 and the second squeezing portion 62 are not fixed to the first blood bag 21 and the second blood bag 22, namely if the surfaces of the first squeezing portion 61 and the second squeezing portion 62 are kept detached from the first blood bag 21 and the second blood bag 22, it is preferred that a medical-purpose lubricant be applied on the surfaces of the first squeezing portion 61 and the second squeezing portion 62 and/or on the surfaces of the first blood bag 21 and the second blood bag 22 in an effort to reduce the frictional forces generated when squeezing the respective blood bags. The connecting portion 63 is arranged between and connected to the first squeezing portion 61 and the second squeezing portion 62.

The motor 70 is used to drive the squeezer 60 and is operated by electric power to rotate in a forward or reverse direction. The motor 70 has an output shaft coupled to a speed reducer 75. The speed reducer 75 serves to reduce the rotation speed of the motor 70 while increasing the torque thereof and includes a plurality of gears. The speed reducer 75 has an output shaft fixed to one end of the connecting portion 63. The other end of the connecting portion 63 is rotatably supported by a bearing (not shown). In FIGS. 3 and 4, the axis of the output shaft of the speed reducer 75 is indicated by an imaginary line.

If the motor 70 rotates in the reverse direction in the state shown in FIG. 6, the squeezer 60 is rotated counterclockwise, thereby squeezing the second blood bag 22 as illustrated in FIG. 7. On the other hand, if the motor 70 rotates in the forward direction in the state illustrated in FIG. 7, the squeezer 60 is rotated clockwise, thereby squeezing the first blood bag 21 as shown in FIG. 6. In the present embodiment, it may be possible to provide an encoder (not shown) for measuring the rotation angle of the motor 70. Moreover, it may be possible to provide a distance measuring sensor (not shown) for measuring the moving distance of the first squeezing portion 61 and the second squeezing portion 62 from a predetermined reference position, e.g., a position where the first blood bag 21 and the second blood bag 22 are equally deformed by the squeezer 60.

The case 80 forms an outer shell of the ventricular assist device in cooperation with the connecting portion 13 of the inlet connector 10 and the connecting portion 33 of the outlet connector 30. The case 80 is made of a polymeric material having superior rigidity and biocompatibility, e.g., polycarbonate, or metal alloy having superior biocompatibility, e.g., stainless steel or titanium alloy. The case 80 includes a first case member 81 and a second case member 82 which are combined together.

The first blood bag 21, the second blood bag 22, the squeezer 60, the motor 70 and the speed reducer 75 are arranged within the case 80. The inlet connector 10 and the outlet connector 30 are inserted into the case 80. Seal members such as O-rings or silicon sealants are interposed between the inlet connector 10 and the case 80 and between the outlet connector 30 and the case 80 in order to prevent generation of gaps. As a result, a completely-isolated airtight space is formed within the case 80.

In addition, the ventricular assist device 100 includes a controller (not shown) for controlling the rotation amount of the motor 70 in response to a signal outputted from the encoder or a signal outputted from the distance measuring sensor and a power supply unit (not shown) for supplying electric power to the motor 70, the encoder and the distance measuring sensor.

Next, description will be made on the operation of the ventricular assist device 100 configured as above.

Upon operating the motor 70, one of the first blood bag 21 and the second blood bag 22 is squeezed by the squeezer 60. If the first squeezing portion 61 squeezes the first blood bag 21, the volume of the first blood bag 21 is reduced and the internal pressure of the first blood bag 21 is increased. The first inlet valve 41 acts to close the first outlet flow path 11 and the first outlet valve 51 acts to open the first inlet flow path 31. Thus the blood stored in the first blood bag 21 is ejected through the outlet flow path of the outlet connector 30 and the outlet conduit 34 and is supplied to the artery 2. At this time, the ejected blood does not flow into the second blood bag 22 due to the existence of the second outlet valve 52.

If the squeezer 60 is rotated at a specified angle, e.g., to the position shown in FIG. 6 and if a predetermined amount of blood is ejected from the first blood bag 21, the motor 70 begins to rotate in the reverse direction, thereby causing the squeezer 60 to rotate counterclockwise. In response, the second squeezing portion 62 begins to squeeze the second blood bag 22.

Upon squeezing the second blood bag 22, the volume of the second blood bag 22 is reduced and the internal pressure of the second blood bag 22 is increased as is the case in the first blood bag 21. The blood stored in the second blood bag 22 is ejected so as to flow out through the outlet flow path of the outlet connector 30.

Simultaneously with the ejection of blood from the second blood bag 22, the blood flows into the first blood bag 21. This is because a negative pressure is generated within the case 80 to compensate the volume reduction of the second blood bag 22. More specifically, the internal space of the case 80 is hermetically sealed and the volume of the internal space of the case 80 is kept constant. Therefore, if the volume of the second blood bag 22 is reduced by squeezing the second blood bag 22, a negative pressure is momentarily generated within the case 80 in proportion to the volume reduction of the second blood bag 22. The squeezed first blood bag 21 is inflated under the action of the negative pressure. Eventually, the internal pressure of the first blood bag 21 grows lower whereby the first inlet valve 41 is operated to open the first outlet flow path 11 of the inlet connector 10. Thus the blood flows into the first blood bag 21.

In case where the first blood bag 21 is made of an elastically deformable material, the first blood bag 21 is elastically restored to an original shape upon releasing the pressure applied to the first blood bag 21. Thus the volume of the internal space of the first blood bag 21 gets increased and the blood flows into the first blood bag 21.

If the second blood bag 22 is squeezed in the manner stated above, the blood is ejected from the second blood bag 22. At the same time, the blood flows into the first blood bag 21. If the squeezer 60 is rotated at a specified angle, e.g., to the position shown in FIG. 7 and if a predetermined amount of blood is ejected from the second blood bag 22, the motor 70 begins to rotate in the forward direction, thereby causing the squeezer 60 to rotate clockwise. In response, the blood stored in the first blood bag 21 is ejected and the blood is allowed to flow into the second blood bag 22.

In the ventricular assist device 100 of the present embodiment described above, the first blood bag 21 and the second blood bag 22 are alternately squeezed to eject the blood in response to the forward and reverse rotation of the motor 70. If a negative pressure is generated by squeezing one of the blood bags, the blood flows into the other blood bag. This eliminates the need to provide a volume compensator or a vent line extending to the outside of the body. Accordingly, it is possible to simplify the configuration of the ventricular assist device and to sharply reduce the risk of infection.

Since the first blood bag 21 and the second blood bag 22 are alternately squeezed to allow the blood to flow into the non-squeezed blood bag, the blood flows into and flow out from the ventricular assist device 100 at all times. This helps prevent the blood from being momentarily stagnant. As a consequence, it is possible to effectively increase the flow rate of the blood.

Inasmuch as the motor 70, the speed reducer 75 and the squeezer 60 are arranged between the first blood bag 21 and the second blood bag 22 in an optimized pattern, there exists no unnecessary space within the case 80. The surfaces of the first squeezing portion 61 and the second squeezing portion 62 are formed into a curved surface shape. Therefore, even if the squeezer 60 is rotated at a minimum angle, it is possible to squeeze the blood bags to a maximum extent. Consequently, it is possible to optimize the size of the ventricular assist device 100. This contributes to the effective use of the ventricular assist device 100 as an implant-type ventricular assist device. The ventricular assist device 100 may be used in an extracorporeal or paracorporeal application.

The power of the motor 70 is transmitted only through the speed reducer 75 without having to use a cam, a crank and the like. This makes it possible to reduce the number of parts and to simplify the power transmitting mechanism. Accordingly, it is possible to greatly increase the durability and the reliability of the ventricular assist device 100.

Since the operation of the motor 70 can be controlled using the signals outputted from the encoder and the distance measuring sensor, it is possible to adjust the squeezing force with which the first blood bag 21 and the second blood bag 22 are squeezed by the first squeezing portion 61 and the second squeezing portion 62. By controlling the motor 70 in this manner, it is possible to easily control the amount of blood ejected at one squeezing time. More specifically, if the rotation angle of the squeezer 60 is reduced, the once-ejected amount of blood grows smaller. If the rotation angle of the squeezer 60 is increased, the once-ejected amount of blood grows larger. Accordingly, the pulsating frequency and the blood ejecting amount can be flexibly adjusted in conformity with the condition of a patient by reducing the once-ejected amount and increasing the pulsating frequency or by increasing the once-ejected amount and reducing the pulsating frequency. It is also possible to control the ejected blood amount so that the blood amount ejected from the first blood bag 21 can differ from the blood amount ejected from the second blood bag 22.

Even when the ventricular assist device 100 of the present embodiment is used as a pneumatically-operated implant-type ventricular assist device, there is no need to provide an additional air pressure line extending to the outside of the body. If a wireless energy signal transmitting device is used, it is possible remove all kinds of lines penetrating the skin.

While the ventricular assist device 100 of the present embodiment is configured to assist the left or right ventricle, it may be possible to configure the ventricular assist device 100 to assist both the left ventricle and the right ventricle. The ventricular assist device 100 of the present disclosure may further include a buffer bag (not shown). The buffer bag is made of a volume-changeable material, preferably an inflatable material. The buffer bag may be installed inside or outside the inlet connector 10. The buffer bag is connected at one side to the ventricle and at the other side to the inlet flow path of the inlet connector 10. The blood flowing out from the ventricle is stored within the buffer bag. The blood stored in the buffer bag flows into the first blood bag 21 or the second blood bag 22 through the inlet connector 10. The buffer bag is fully filled with the blood. The amount of blood filled in the buffer bag is increased or decreased as the buffer bag is inflated or deflated. The buffer bag stores the blood in an amount greater than the amount once-ejected by the ventricular assist device 100. Even in an emergency situation where the amount of blood flowing out from the ventricle is temporarily decreased, it is possible for the buffer bag to supply a constant amount of blood to the first blood bag 21 or the second blood bag 22. More specifically, if the amount of blood flowing from the ventricle is decreased, the buffer bag supplies an increased amount of blood to the first blood bag 21 or the second blood bag 22. As the volume of blood flowing out from the buffer bag becomes greater than the volume of blood flowing into the buffer bag, the buffer bag is deflated to have a reduced volume.

Provision of the buffer bag enables the ventricular assist device 100 to continuously eject a constant amount of blood even in an emergency situation where the amount of blood flowing out from the ventricle is decreased. Thanks to this feature, the ventricular assist device 100 is free from a so-called "suction" problem, which makes it possible to enhance the stability and the reliability of the device.

Figure 9:
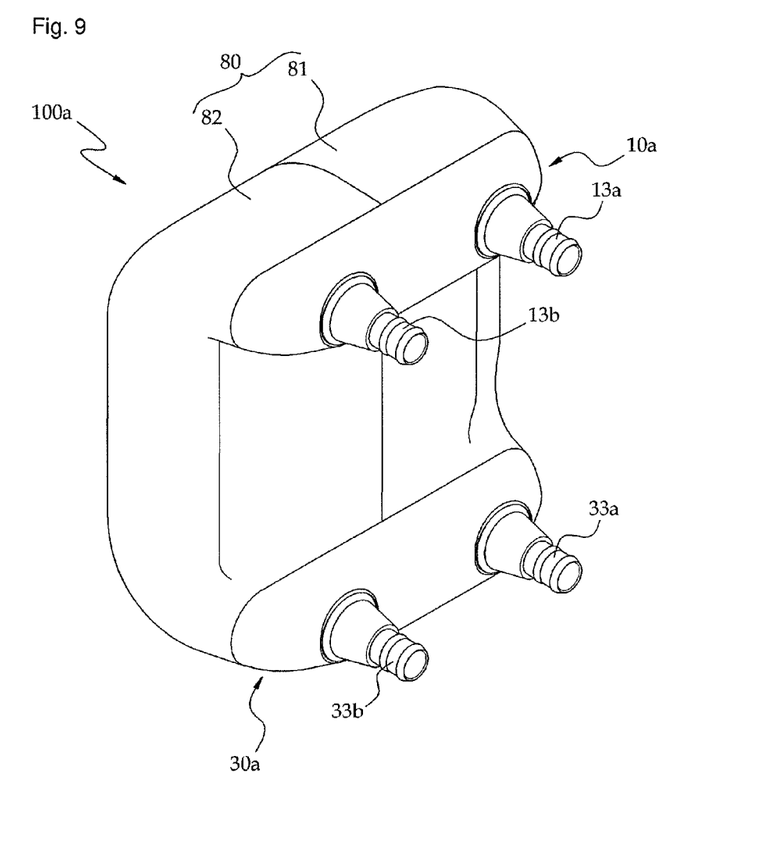
FIG. 9 is a schematic perspective view showing a ventricular assist device according to another embodiment of the present invention.
Figure 10:
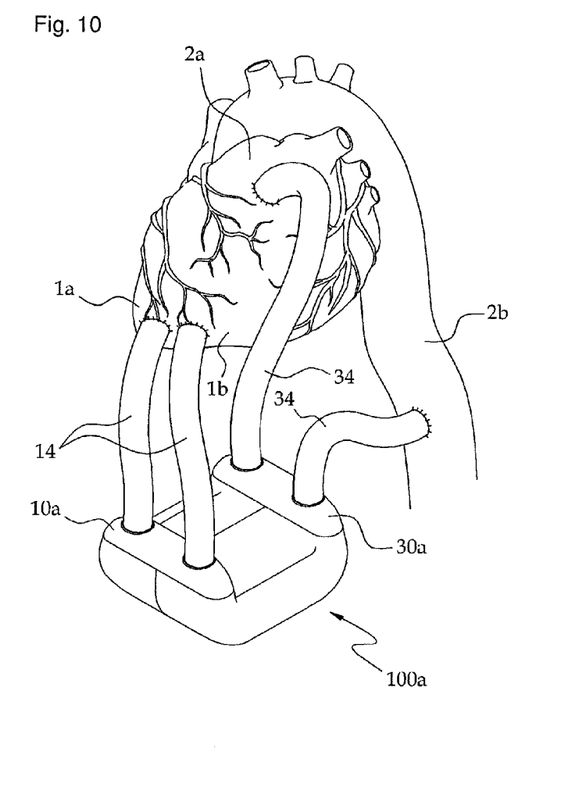
FIG. 10 is a perspective view schematically showing how the ventricular assist device shown in FIG. 9 is installed within a human body.

FIGS. 9 and 10 show a ventricular assist device according to another embodiment of the present invention. Referring to FIGS. 9 and 10, the ventricular assist device 100a includes an inlet connector 10a having a first inlet flow path (not shown) and a second inlet flow path (not shown) which are formed independently of each other. The inlet connector 10a includes a first connecting portion 13a and a second connecting portion 13b. Inlet conduits 14 are fitted to the first connecting portion 13a and the second connecting portion 13b. The inlet conduits 14 are connected to the left ventricle 1a and the right ventricle 1b and are also connected to the first inlet flow path and the second inlet flow path. The first inlet flow path and the second inlet flow path lead to the first blood bag and the second blood bag. A first inlet valve and a second inlet valve are installed in the first inlet flow path and the second inlet flow path.

The ventricular assist device 100a includes an outlet connector 30a having a first outlet flow path (not shown) and a second outlet flow path (not shown) which are formed independently of each other. The outlet connector 30a includes a first connecting portion 33a and a second connecting portion 33b. Outlet conduits 34 are fitted to the first connecting portion 33a and the second connecting portion 33b. The outlet conduits 34 are connected to the aorta 2a and the pulmonary artery 2b and are also connected to the first outlet flow path and the second outlet flow path. The first outlet flow path and the second outlet flow path lead to the first blood bag and the second blood bag. A first outlet valve and a second outlet valve are installed in the first inlet flow path and the second inlet flow path.

As can be appreciated in FIG. 10, the ventricular assist device 100a of the present embodiment serves as a biventricular assist device capable of assisting both the left ventricle and the right ventricle.

Figure 11:
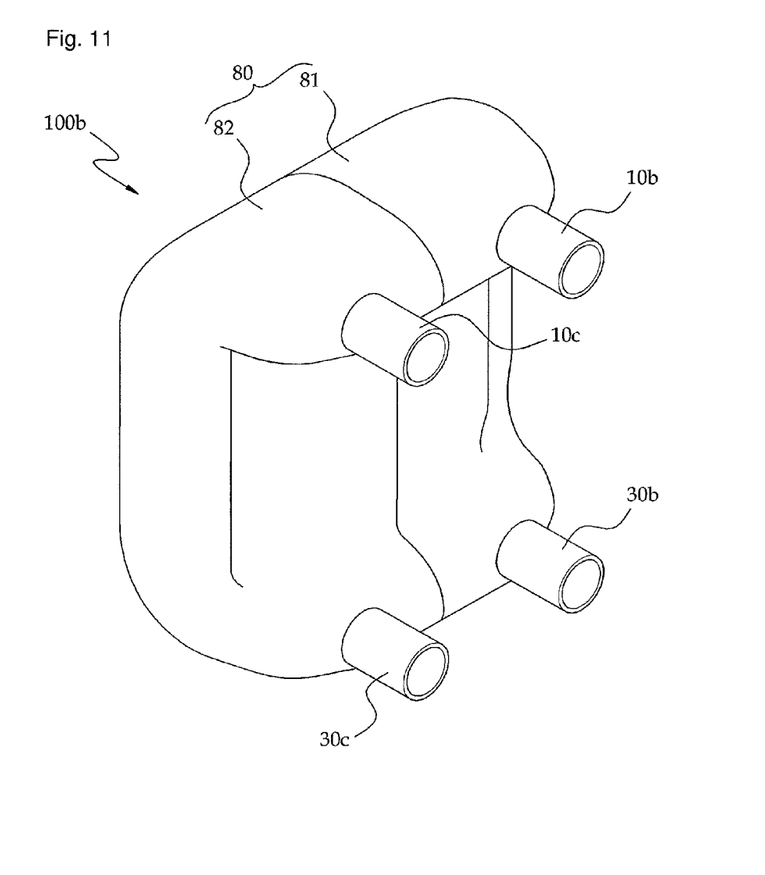
FIG. 11 is a schematic perspective view showing a ventricular assist device according to a further embodiment of the present invention.

FIG. 11 is a schematic perspective view showing a ventricular assist device according to a further embodiment of the present invention. Referring to FIG. 11, the ventricular assist device 100b includes a first inlet pipe 10b and a second inlet pipe 10c, both of which serve as a first inlet flow path and a second inlet flow path. The ventricular assist device 100b further includes a first outlet pipe 30b and a second outlet pipe 30c, both of which serve as a first outlet flow path and a second outlet flow path. The first blood bag is connected to the first inlet pipe 10b and the first outlet pipe 30b. The second blood bag is connected to the second inlet pipe 10c and the second outlet pipe 30c.

While certain preferred embodiment of the invention has been described hereinabove, the present invention is not limited thereto. It is to be understood that various changes and modifications may be made without departing from the scope of the invention defined in the claims.

What is claimed is:

1. A ventricular assist device, comprising:
a case;
a pair of blood bags installed inside the case, each of the blood bags including an inlet port connected to a ventricle of a heart to introduce therethrough blood flowing out from the ventricle, an internal space formed to store the blood introduced through the inlet port and an outlet port connected to an artery to discharge therethrough the blood stored in the internal space, the internal space having a variable volume; and
a squeezing unit installed inside the case, the squeezing unit configured to alternately squeeze the blood bags in such a way that, if one of the blood bags is squeezed to discharge the blood, the other blood bag is inflated to draw the blood,
wherein the squeezing unit includes a motor and a squeezer connected to and driven by the motor, the squeezer configured to, when driven, alternately squeeze the blood bags,
wherein the motor is configured to rotate in a forward direction and a reverse direction, the squeezer configured to squeeze one of the blood bags when the motor rotates in the forward direction and to squeeze the other blood bag when the motor rotates in the reverse direction.

2. The ventricular assist device of claim 1, wherein the squeezer includes a pair of squeezing portions configured to make contact with the blood bags and squeeze the blood bags when the motor rotates in the forward direction and the reverse direction and a connecting portion arranged between the squeezing portions, the connecting portion connected to the squeezing portions and the motor.

3. The ventricular assist device of claim 2, wherein each of the squeezing portions making contact with the blood bags has a surface of curved surface shape bulging toward each of the blood bags.

4. The ventricular assist device of claim 2, wherein the squeezing portions extending in a longitudinal direction, each of the squeezing portions including a bulging portion having a substantially semicircular cross section taken along a plane perpendicular to the longitudinal direction.

5. The ventricular assist device of claim 2, wherein a lubricant is applied on surfaces of the squeezing portions making contact with the blood bags or on surfaces of the blood bags making contact with the squeezing portions.

6. The ventricular assist device of claim 2, wherein the squeezing portions are fixed to the blood bags.

7. A ventricular assist device, comprising:
a case;
a pair of blood bags installed inside the case, each of the blood bags including an inlet port connected to a ventricle of a heart to introduce therethrough blood flowing out from the ventricle, an internal space formed to store the blood introduced through the inlet port and an outlet port connected to an artery to discharge therethrough the blood stored in the internal space, the internal space having a variable volume; and
a squeezing unit installed inside the case, the squeezing unit configured to alternately squeeze the blood bags in such a way that, if one of the blood bags is squeezed to discharge the blood, the other blood bag is inflated to draw the blood, wherein the squeezing unit includes a motor and a squeezer connected to and driven by the motor, the squeezer configured to, when driven, alternately squeeze the blood bags, wherein the squeezing unit further includes a speed reducer connected to the motor and the squeezer, the speed reducer configured to transmit a rotation force of the motor to the squeezer at a reduced rotation speed.

8. The ventricular assist device of claim 1, further comprising: an inlet connector coupled to the case, the inlet connector including an inlet flow path connected to the ventricle to introduce therethrough the blood from the ventricle and a pair of outlet flow paths respectively connected to the inlet flow path and the inlet ports of the blood bags; an outlet connector coupled to the case, the outlet connector including a pair of inlet flow paths respectively connected to the outlet ports of the blood bags and an outlet flow path connected to the inlet flow paths of the outlet connector and the artery; a pair of inlet valves respectively provided in the outlet flow paths of the inlet connector, the inlet valves configured to permit flow of the blood from the inlet flow path of the inlet connector toward the blood bags while preventing back flow of the blood; and a pair of outlet valves respectively provided in the inlet flow paths of the outlet connector, the outlet valves configured to permit flow of the blood from the blood bags toward the outlet flow path of the outlet connector while preventing back flow of the blood.

9. The ventricular assist device of claim 1, further comprising: a pair of inlet pipes coupled to the case, the inlet pipes connected to the ventricle to introduce therethrough the blood from the ventricle and also respectively connected to the inlet ports of the blood bags; a pair of outlet pipes coupled to the case, the outlet pipes respectively connected to the outlet ports of the blood bags and also connected to the artery; a pair of inlet valves respectively provided in the inlet pipes, the inlet valves configured to permit flow of the blood from the inlet pipes toward the blood bags while preventing back flow of the blood; and a pair of outlet valves respectively provided in the outlet pipes, the outlet valves configured to permit flow of the blood from the blood bags toward the outlet pipes while preventing back flow of the blood.

10. The ventricular assist device of claim 1, wherein the case has a hermetically sealed internal space, the blood bags arranged in the internal space of the case.

11. A ventricular assist device, comprising:

a case;

a pair of blood bags installed inside the case, each of the blood bags including an inlet port connected to a ventricle of a heart to introduce therethrough blood flowing out from the ventricle, an internal space formed to store the blood introduced through the inlet port and an outlet port connected to an artery to discharge therethrough the blood stored in the internal space, the internal space having a variable volume;

a squeezing unit installed inside the case, the squeezing unit configured to alternately squeeze the blood bags in such a way that, if one of the blood bags is squeezed to discharge the blood, the other blood bag is inflated to draw the blood; and a buffer bag made of an inflatable material, the buffer bag connected to the ventricle and configured to store the blood introduced from the ventricle, the buffer bag connected to the inlet ports of the blood bags to supply the blood stored in the buffer bag to the blood bags.

12. The ventricular assist device of claim 1, further comprising: a controller configured to control the motor in such a way as to adjust a volume of the blood flowing out from the blood bags.

* * * * *